United States Patent [19]
Kobayashi et al.

[11] Patent Number: 5,445,950
[45] Date of Patent: Aug. 29, 1995

[54] METHOD OF USING α-AMYLASE TO PREPARE SLIGHTLY DECOMPOSED STARCH GRANULES HAVING LOW VISCOSITY

[75] Inventors: Shoichi Kobayashi, Tsuchiura; Shoji Miwa; Wakako Tsuzuki, both of Tsukuba, all of Japan

[73] Assignee: Director of National Food Research Institute Ministry of Agriculture, Forestry and Fisheries, Tsukuba, Japan

[21] Appl. No.: 349,478

[22] Filed: Dec. 2, 1994

Related U.S. Application Data

[63] Continuation of Ser. No. 122,135, Sep. 15, 1993, abandoned, which is a continuation of Ser. No. 936,892, Aug. 27, 1992, abandoned.

[30] Foreign Application Priority Data

Oct. 31, 1991 [JP] Japan ................. 3-311509

[51] Int. Cl.[6] .................. C12P 19/14; C12P 19/04
[52] U.S. Cl. ........................ 435/99; 435/101
[58] Field of Search ................... 435/99, 101

[56] References Cited

U.S. PATENT DOCUMENTS

| | | | |
|---|---|---|---|
| 4,933,279 | 6/1990 | Carroll et al. | 435/99 |
| 5,180,669 | 1/1993 | Andrim | 435/99 |
| 5,322,778 | 6/1994 | Antrim et al. | 435/99 |

FOREIGN PATENT DOCUMENTS

| | | |
|---|---|---|
| 0182296 | 5/1986 | European Pat. Off. |
| 46-14706 | of 1971 | Japan . |
| 64-30583 | of 1989 | Japan . |
| 1-174394 | of 1989 | Japan . |
| WO89/04842 | 6/1989 | WIPO . |

OTHER PUBLICATIONS

H. Fuwa et al, "Susceptibility of Various Starch Granules to Amylases as Seen by Scanning Electron Microscope", Starch/Starke, vol. 30, No. 6, 1978, pp. 186–191.

Primary Examiner—David M. Naff
Assistant Examiner—Francisco C. Prats
Attorney, Agent, or Firm—Frishauf, Holtz, Goodman, Langer & Chick

[57] ABSTRACT

A method is provided for producing modified starch granules having low viscosity and being capable of absorbing hydrophobic substances. The modified starch granules are prepared by contacting raw starch granules with an α-amylase and/or glucoamylase the modified starch granules are prepared at 10° to 65° C. to a decomposition percentage of 0.1 to 15%, preferably 0.1 to 1.0%. When cereal starch granules are lightly decomposed with α-amylase, the viscosity of the granules decreases to such a degree that they are only slightly viscous. The decomposed starch granules may be used in preparing instant liquid foods. By appropriately blending the decomposed starch granules and other non-treated starch granules or other decomposed starch granules, blends of different starch granules having various viscosities can be obtained. The paste or liquid prepared from the enzyme-treated starch granules is smooth and soft to the touch and are useful as base materials for producing various foods. The modified starch granules having low viscosity may be combined with starch granules containing adsorbed aromatic components to produce various foods. Since the enzyme-treated low-viscosity starch granules may be easily produced, they are useful as a raw material in the starch sugar industry.

7 Claims, 2 Drawing Sheets

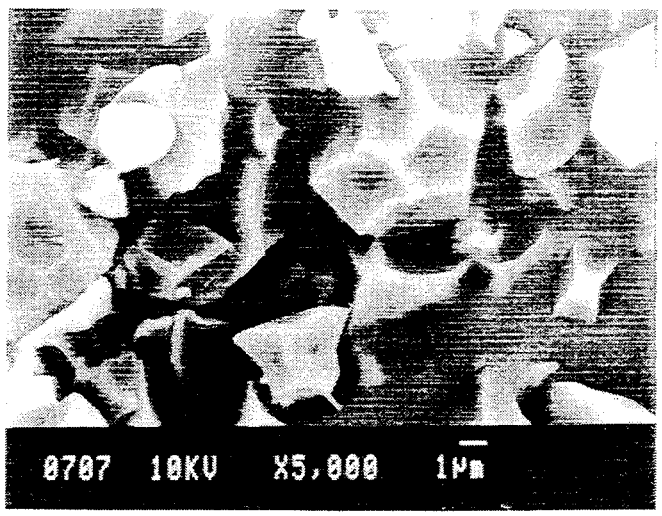
FIG. IA
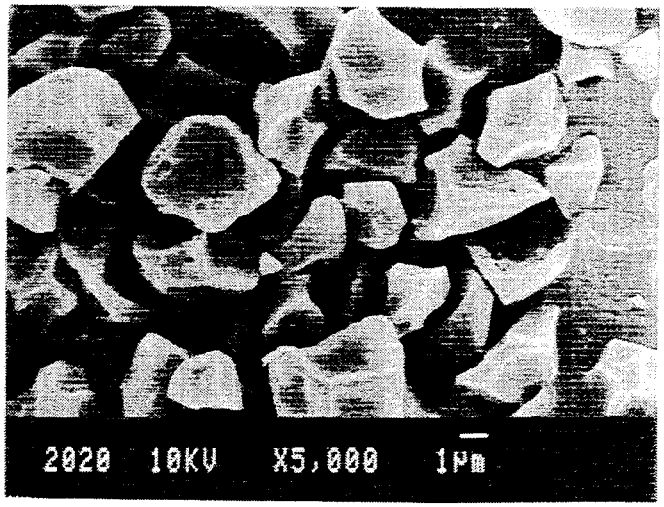
FIG. IB
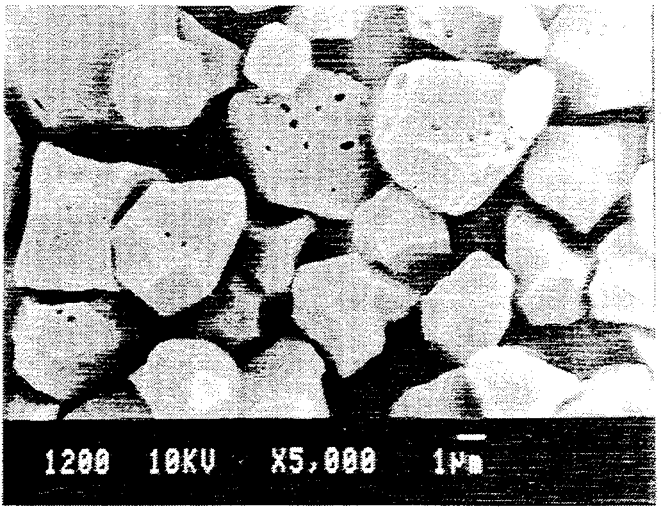
FIG. IC

METHOD OF USING α-AMYLASE TO PREPARE SLIGHTLY DECOMPOSED STARCH GRANULES HAVING LOW VISCOSITY

This application is a Continuation of application Ser. No. 08/122,135, filed Sep. 15, 1993 (abandoned), which is a continuation of application Ser. No. 07/936,892 filed Aug. 27, 1992 (abandoned).

The present invention relates to a method of preparing starch granules having modified characteristics. More precisely, it relates to a method of preparing modified starch granules, in which starch granules are treated with various amylases to modify the characteristics of the starch granules.

BACKGROUND OF THE INVENTION

For improving and modifying physical properties of starch, heretofore, there was known a method of adding an α-amylase or acid to starch, when starch is blended with water for gelatinization, so as to lower the viscosity of the blend. There was also known a method of adding various substances such as a metal ion, an algal polysaccharide or a water-soluble gum to starch so as to elevate or lower the physical properties of the starch gel. For modifying the characteristics of starch granules, there was known a method of crosslinking starch granules to make the starch granules less soluble.

However, a method has heretofore been unknown, in which starch granules are directly treated with an enzyme to modify the characteristics of the granules, whereby the physical properties of the granules are noticeably varied when dissolved in water. It was heretofore not known how greatly the physical properties of starch granules would vary when the starch granules are dissolved in water when they are treated with enzymes of certain kinds. It was heretofore not known that the physical properties of starch granules would vary greatly by such treatment.

SUMMARY OF THE INVENTION

The present inventors variously investigated so as to modify the characteristics of starch granules by directly treating starch granules with an enzyme and, as a result, have found that the intended object can be attained by treating starch granules with an amylase.

Specifically, after they treated starch granules with various amylases such as α-amylase, β-amylase or glucoamylase, took out the enzyme-treated starch granules and investigated the physical properties of them, they have found that the enzyme-treated starch granules displayed various physical properties when dissolved, depending upon the kind of the enzyme used for treatment and the kind of the starch granules to be treated therewith. On the basis of the finding, they have completed the present invention.

Accordingly, the present invention relates to a method of preparing starch granules with modified characteristics, in which starch granules are treated with an amylase.

DESCRIPTION OF THE DRAWINGS

FIG. 1 shows photographs of α-amylase-treated rice starch granules "Wakaho-no-minori", as taken with a scanning electromicroscope; in which A is a control sample (decomposition percentage, 0%), B is a sample with a decomposition percentage of 2.0%, and C is a sample with a decomposition percentage of 5.0%.

DETAILED DESCRIPTION OF THE INVENTION

Figure 2:
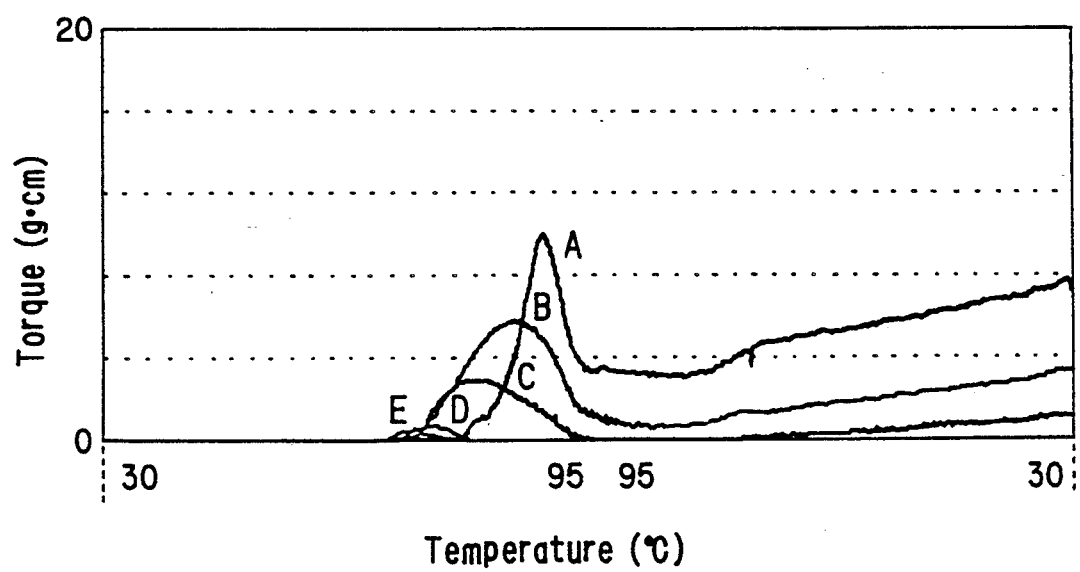
FIG. 2 shows a viscograph of α-amylase-treated rice starch granules "Nihon-bare", in which A is a control sample (decomposition percentage, 0%), B is a sample with a decomposition percentage of 0.5%, C is a sample with a decomposition percentage of 0.9%, D is a sample with a decomposition percentage of 1.9%, and E is a sample with a decomposition percentage of 3.1%.

In the present invention, any starch granules from various sources may be used, such as those from rice, wheat, corn, potato and sweet potato.

As amylases for decomposition of such starch granules in accordance with the present invention, any one derived from various sources can be used. Generally used are commercial products, such as a purified α-amylase (produced by Sigma Co., derived from *Bacillus amyloliquefaciens*, with 930 IU(international unit)/mg), a purified glucoamylase (produced by Seikagaku KK, derived from *Rhizopus niveus*, with 32.6 IU/mg), and a purified β-amylase (produced by Sigma Co., derived from TYPE1-B sweet potato, with 965 IU/mg). In treatment of starch granules with the enzyme, where the pH variation in the reaction system is small, use of any particular buffer would be unnecessary. As the case may be, various buffers can be used such as a phosphoric acid buffer(pH6.9), an acetic acid buffer (pH5.2), and an acetic acid buffer (pH2.8).

The enzymatic treatment of starch granules is to be effected in such a way that the starch granules are not over-decomposed. In general, it is effected in the manner that starch granules are decomposed to have a decomposition percentage of from 0.1 to 15.0%. The concentration of the starch granules which are the substrate for the enzymatic treatment may be such that the granules are suspended or are in the form of a cake, preferably, it is from 5 to 40%. The amount of the amylase to be used for the enzymatic treatment varies, depending upon the kind of the starch granules to be treated therewith and the kind of the enzyme itself. For instance, where the above-mentioned purified α-amylase (produced by Sigma Co., derived from *Bacillus amyloliquefaciens*) is used, it is added to the reaction system in an amount of from 0.4 to 400 IU, preferably from 4 to 40 IU, per g of starch granules to be treated therewith. The enzymatic reaction is effected in the above-mentioned buffer or in water under the following conditions: at a temperature of from 10 to 65° C., preferably from 25 to 40° C., for 1 to 4 hours. Where the enzymatic reaction needs a long period of time, the amount of the enzyme to be added thereto may be reduced. The enzyme titer is herein identified by the Somogyi-Nelson method; and the decomposition percentage of the starch granules treated is herein determined by sampling the decomposed starch suspension at regular intervals, centrifuging it at 3,000 rpm for 10 minutes, and measuring the free saccharide as liberated in the resulting supernatant by a phenol-sulfuric acid method. On the basis of the thus measured value, the intended decomposition percentage of all the starch granules treated is calculated.

The present invention will be explained in more detail by way of the following examples, which, however, are not intended to restrict the scope of the present invention.

In the following examples, the scanning electromicroscopic (SEM) observation was effected in the manner mentioned below. The precipitates to be used for measurement of the decomposition percentage of the decomposed starch suspension, which is sampled at regular intervals, are isolated by centrifugation (3,000 rpm, 10 min), washed twice with distilled water and once with acetone and dried. The dried powder is sprinkled over a sample stand having a duplicate-adhesive tape attached thereto, and this is coated with gold (200 Å thick) by gold vapor deposition with an ion-sputtering device (JFC-1500 Model, manufactured by Nippon Electronic Co.). The sample preparation is then observed with SEM of JSM-880 Model (manufactured by Nippon Electronic Co.) under the condition of an accelerated voltage of from 3 to 10 KV and a magnification of from 500 to 2,000 times.

Measurement of the viscosity of each sample is effected with a microviscograph (manufactured by Toyoh Seiki Seisakusho KK). Briefly, enzyme-treated rice starch grains as previously determined with respect to the water content thereof are adjusted to be 8% dried, and the variation of the viscosity of 10g of an aqueous suspension of the rice starch grains is measured. The conditions for the measurement are such that the start temperature and the final temperature are both 30° C., The start temperature retention time is 5 minutes; the heating and cooling rate is 1.5° C./min, the higher most critical temperature is 99° C.(whereupon the temperature of the sample is 95° C.); the higher most critical temperature retention time is 10 minutes, the rotation number with torque detection blade A type is 75 rpm, and the torque range is 20 and 50 g.cm. Display of the viscosity curve is effected with TS viscograph software.

The rice samples used include five kinds of polished rice of "Wakaho-no-megumi", "Wakaho-no-minori" and "Nihon-bare" as produced in Saitama-ken in 1990; and "Koshihikari (trade name: Pearl Rice Ten-keimai)'-'and "Mochihikari (trade name: Pearl Rice Mochigome)" as produced in Nagano-ken in 1990. These are purified by an alkaline method (with 0.25 % sodium hydroxide) and dried under pressure at 40° C. to prepare starch granules, which are used. Commercial products of corn starch, potato starch, wheat starch and sweet potato starch samples are used.

EXAMPLE 1

Regarding the enzyme decomposability of rice starch grains, enzyme decomposition conditions of rice samples of the above-mentioned five kinds with α-amylase, glucoamylase and β-amylase are shown in Table 1 below.

TABLE 1

| Enzyme Decomposition Conditions of Rice Starch Grains | | | | |
|---|---|---|---|---|
| Name of Enzyme | Determined Decomposition Percentage (%) | Amount of Starch (g) | Amount of Enzyme (mg) | Amount of Buffer (ml) | Decomposition Time (hr) |
| α-amylase | 0.5 | 25 | 0.01 | 100 | 0.5~2.5 |
|  | 1.0 | 25 | 0.10 | 100 | 1.0 |
|  | 2.0 | 25 | 1.00 | 100 | 1.0~3.5 |
|  | 3.0 | 25 | 5.00 | 100 | 2.0~4.0 |
|  | 5.0 | 25 | 5.00 | 100 | 2.0~4.0 |
| gluco-amylase | 0.5 | 25 | 1.00 | 100 | 1.0~5.5 |
|  | 2.0 | 25 | 1.00 | 100 | 1.0~5.5 |
|  | 2.5 | 25 | 2.00 | 100 | 2.0~8.0 |
|  | 5.0 | 25 | 2.0 | 100 | 2.0~8.0 |
|  | *30.0 | 25 | 10 ml | 100 | 9. |
| β- | 0.4 | 10 | 0.01 | 50 | 4. |
|  | 0.8 | 10 | 1 ml | 25 | 4 |

TABLE 1-continued

| Enzyme Decomposition Conditions of Rice Starch Grains | | | | |
|---|---|---|---|---|
| Name of Enzyme | Determined Decomposition Percentage (%) | Amount of Starch (g) | Amount of Enzyme (mg) | Amount of Buffer (ml) | Decomposition Time (hr) |
| amylase | | | | | |

(*) Industrial crude enzyme liquid was used.

The difference in the enzyme decomposability with α-amylase between rice starch granules of different kinds was investigated with respect to the time-dependent variation thereof in a low decomposition percentage range (1 to 9%) and in a high decomposition percentage range (8 to 27%) to give a result that the enzyme decomposability of "Mochihikari" was high and that of "Nihon-bare" was low in both the low decomposition percentage range and the high decomposition percentage range. Regarding the difference in the decomposability between the other kinds, "Wakaho-no-megumi" and "Wakaho-no-minori" had the highest decomposability, then "Koshihikari" in this order, in the low decomposition percentage range, while there was almost no difference between "Wakaho-no-megumi" and "Wakaho-no-minori" in this respect. In the high decomposition range, "Wakaho-no-megumi" had the highest decomposability, then "wakaho-no-minori" and then "koshihikari" in this order, but the difference between them was not so large.

With respect to glucoamylase, there was almost no difference in the decomposability between rice starch granules of different kinds.

With respect to β-amylase, a large amount of concentrated pure enzyme liquid thereof was added to the reaction system, but the enzyme decomposability thereof of decomposing rice starch grains was weak.

In every enzyme tested, there was admitted no relationship between the protein and amylose content therein and the enzyme decomposability.

Rice starch granules as decomposed by α-amylase in a decomposition percentage of 0%, 2% and 5 % were observed by SEM, and the photographs taken are shown in FIG. 1.

The outward appearance of the rice starch grains as decomposed with the enzyme in a decomposition percentage of 1 to 2% was not specifically different from that of the non-treated rice starch granules. However, the rice starch grains as decomposed with it in a decomposition percentage of 5% gave definite holes. With elevation of the decomposition percentage, the number of the holes on the surface of the decomposed starch granules and the size of them increased. The starch granules were admitted to be destroyed in a decomposition percentage of 20%; and a fairly large number of starch granules were destroyed in a decomposition percentage of 25%.

Also in the case of glucoamylase, the number of the holes and the size of them on the surface of the decomposed starch granules increased with elevation of the decomposition percentage. However, when glucoamylase was compared with α-amylase with respect to the decomposability in the same decomposition percentage, the size of the holes as made with glucoamylase was smaller than that with α-amylase. Even in the decomposition percentage of 30%, the number of the holes and the size of them increased with glucoamylase, but the shape of the decomposed starch granules was not destroyed, but was maintained as it was.

However, decomposition with β-amylase was weak, and both the number of the holes and the size of them made in rice starch granules of all the kinds as decomposed with it were small.

As mentioned above, the enzyme decomposability varies, depending upon the kind of the enzyme used and the kind and sort of the starch granules decomposed therewith. However, the difference between the decomposability and the physical properties was not clarified up to date. The physical properties of the enzyme-treated starch granules were investigated with a viscograph and, as a result, it was clarified for the first time that there was a great difference in the physical properties, even though the decomposition ratio is the same.

A viscogram of each of the enzyme-treated rice starch granules of all the above-mentioned kinds was taken. As one typical example, the viscogram of "Nihon-bare" as decomposed with α-amylase is shown in FIG. 2 As is obvious from it, an extreme change is admitted even in the starch granules which are same as the non-treated ones with respect to the outward appearance.

Regarding the characteristic of the variation of the viscosity of α-amylase-decomposed starch granules, the maximum viscosity and the minimum viscosity, as well as the final viscosity were decreased even by a weak enzymatic decomposition of 0.5% or so as to often cause noticeable decrease of break-down, consistency and setback. In the decomposition percentage of 2%, the characteristic values greatly decrease; and in the decomposition percentage of 3% and 5%, the rice starch granules of almost all the kinds lost gelatinization and aging. With increase of the decomposition percentage, the tendency was admitted towards elevation of the gelatinization temperature.

With respect to the difference in the kind of rice, "Wakaho-no-megumi" had a noticeable lowering effect of the characteristic values in the decomposition percentage of 0.5% and 0.9%, and it had an extreme lowering effect of them in the decomposition percentage of 2.2% with detection of almost neither gelatinization and aging. "Wakaho-no-minori" had noticeable lowering effect of the characteristic values in the decomposition percentage of 0.5%, and the characteristic values of it gradually lowered with elevation of the decomposition percentage of from 1.% to 2.2%, while slight gelatinization and aging was admitted even in the decomposition percentage of 2.7% and 4.5%. In the case of "Nihonbare", it had noticeably lowered characteristic values in the decomposition percentage of 0.5%. With elevation of the decomposition percentage from 0.9% to 1.9% to 3.1%, the characteristic values gradually lowered, but the difference in the characteristic values between the decomposition percentage of 1.9% and that of 3.1% was small. In the decomposition percentage of 5.1%, both gelatinization and aging disappeared. In the case of "Koshihikari", it had noticeable lowering of the characteristic values in the decomposition percentage of 0.4%, and the characteristic values of it greatly lowered in the decomposition percentage of 1.1%. With elevation of the decomposition percentage of from 1.9% to 2.9%, the characteristic values gradually lowered, and neither gelatinization nor aging was almost detected in the decomposition percentage of 5.2%. On the other hand, in the case of "Mochihikari", it had noticeable lowering of the characteristic values in the decomposition percentage of 0.5%. The characteristic values of it remarkably lowered in the decomposition percentage of 1.0%; and neither gelatinization nor aging was almost admitted in the decomposition percentage of 2.0%, 3.0% and 5.6%.

As will be understood from the above, the variation of the characteristics in the enzyme-decomposed rice starch granules is totally large in a low decomposition percentage range (2% or less), though somewhat varying in accordance with the kinds of rice.

The glucoamylase decomposition and β-amylase decomposition were admitted to have no particular influence on the variation of the viscosity of the decomposed products, irrespective of the degree of the decomposition percentage and the kind of rice used. Only with respect to the glucoamylase decomposition, slight delay of the gelatinization temperature was admitted with increase of the decomposition percentage.

For corn starch, the decomposability with three enzymes of α-amylase, β-amylase and glucoamylase was investigated; and for potato, sweet potato and wheat, the decomposability with α-amylase was investigated. As shown in Table 2, the decomposability of corn and wheat with α-amylase was high, while that of potato and sweet potato with the same was low.

TABLE 2

Viscographic Characterisitic Values of α-amylase-decomposed Starch Granules
Viscographic Characterisitic Values of Glucoamylase-decomposed Rice Starch Granules

| Kind | Decomposition Percentage (%) | Gelatinization Temperature (°C.) | Maximum Viscosity (g · cm) | Maximum Viscosity Temperature (°C.) | Minimum Viscosity (g · cm) | Minimum Viscosity Temperature (°C.) | Break-down | Final Viscosity (g · cm) | Consistency (g · cm) | Set-back (g · cm) |
|---|---|---|---|---|---|---|---|---|---|---|
| Corn | 0.0 | 78.0 | 10.0 | 89.0 | 5.1 | 95.0 | 4.9 | 19.4 | 14.3 | 8.3 |
|  | 0.6 | 70.0 | 9.9 | 83.5 | 5.4 | 94.0 | 4.5 | 22.4 | 17.0 | 5.9 |
|  | 1.1 | 69.0 | 9.4 | 80.5 | 4.5 | 93.5 | 4.9 | 21.0 | 16.5 | 6.2 |
|  | 2.0 | 69.0 | 5.9 | 73.0 | 0.5 | 95.5 | 5.4 | 4.6 | 4.1 | 1.5 |
|  | 3.3 | 69.0 | 5.6 | 73.0 | 0.3 | 95.0 | 5.3 | 4.0 | 3.7 | 1.3 |
|  | 4.3 | 68.5 | 5.1 | 73.0 | 0.2 | 95.0 | 4.9 | 3.0 | 2.8 | 1.0 |
|  | 7.2 | 68.5 | 5.2 | 73.0 | 0.0 | 94.5 | 5.2 | 5.6 | 5.6 | 1.3 |
|  | 9.4 | 67.0 | 1.7 | 71.0 | 0.0 | 95.0 | 1.7 | 0.3 | 0.3 | 0.2 |
|  | 14.0 | 65.0 | 0.4 | 69.0 | 0.0 | 96.0 | 0.4 | 0.1 | 0.1 | 0.0 |
| Potato | 0.0 | 61.0 | 35.0 | 67.5 | 7.5 | 96.0 | 27.5 | 19.0 | 11.5 | 2.5 |
|  | 0.5 | 56.0 | 27.5 | 63.5 | 3.0 | 93.0 | 24.5 | 8.5 | 5.5 | 1.0 |
|  | 0.9 | 54.0 | 27.5 | 64.0 | 3.0 | 94.0 | 24.5 | 8.5 | 5.5 | 0.5 |
|  | 1.3 | 56.0 | 22.5 | 45.0 | 3.0 | 94.0 | 19.5 | 12.5 | 9.5 | 1.5 |
|  | 2.0 | 56.0 | 8.5 | 11.9 | 0.0 | 96.0 | 8.5 | 0.2 | 0.2 | 0.2 |
|  | 2.7 | 55.0 | 3.8 | 58.5 | 0.0 | 95.0 | 3.8 | 0.1 | 0.1 | 0.1 |
| Wheat | 0.0 | 74.0 | 9.4 | 89.0 | 3.6 | 95.0 | 5.8 | 24.0 | 20.4 | 7.9 |
|  | 0.5 | 73.0 | 3.9 | 86.5 | 0.8 | 95.5 | 3.1 | 23.5 | 22.7 | 4.0 |

TABLE 2-continued

| | Viscographic Characterisitic Values of α-amylase-decomposed Starch Granules | | | | | | | | | |
|---|---|---|---|---|---|---|---|---|---|---|
| | Viscographic Characterisitic Values of Glucoamylase-decomposed Rice Starch Granules | | | | | | | | | |
| Kind | Decomposition Percentage (%) | Gelatinization Temperature (°C.) | Maximum Viscosity (g · cm) | Maximum Viscosity Temperature (°C.) | Minimum Viscosity (g · cm) | Minimum Viscosity Temperature (°C.) | Break-down | Final Viscosity (g · cm) | Consistency (g · cm) | Set-back (g · cm) |
| | 0.9 | 76.0 | 3.1 | 86.0 | 0.3 | 95.5 | 2.8 | 21.0 | 20.7 | 2.5 |
| | 2.2 | 70.0 | 2.7 | 84.5 | 0.2 | 95.0 | 2.5 | 13.5 | 13.3 | 2.0 |
| | 3.0 | 69.0 | 1.8 | 83.5 | 0.1 | 95.0 | 1.7 | 9.3 | 9.2 | 0.9 |
| | 5.6 | 68.5 | 1.8 | 83.0 | 0.1 | 95.0 | 1.7 | 7.6 | 7.5 | 0.8 |
| | 7.4 | 68.0 | 1.4 | 81.0 | 0.1 | 95.0 | 1.3 | 6.2 | 6.1 | 0.5 |

The decomposability with glucoamylase and β-amylase was low. Particularly, they were decomposed only slightly with β-amylase.

The thus enzyme-decomposed four kinds of starch granules were observed by SEM. As a result, it was admitted that all the four kinds of starch granules were decomposed with α-amylase with increase of the number of the holes and the size of them along with elevation of the decomposition percentage. In addition, decomposition of corn starch granules with glucoamylase and β-amylase was also admitted.

In determination of the physical properties, noticeable variation of the physical properties was admitted in the four kinds of starch granules as decomposed with α-amylase. Precisely, the variation was remarkable in potato and sweet potato having a decomposition percentage of 2.0% and in wheat having a decomposition percentage of 0.5%; or that is, both the maximum viscosity and the minimum viscosity and the final viscosity lowered and the break-down, consistency and set-back were reduced, but disappearance of gelatinization and aging was not admitted. Also in corn having a decomposition percentage of 2.0%, these characteristic values decreased, and the decrease of them was especially large in the decomposition percentage of 9.4% with disappearance of both gelatinization and aging. However, in the decomposition percentage of from 0.5 to 1% or so, increase of the consistency and the final viscosity was admitted.

Where corn starch granules were decomposed with glucoamylase or β-amylase, no noticeable variation of the viscosity of the decomposed products was not admitted.

From the above-mentioned results, it is understood that since the α-amylase-treated rice and corn starch granules in a decomposition percentage of 2% rapidly liquefy and uniformly dissolve when a hot water is added thereto, they are widely utilizable in instant soup and broth dishes. On the other hand, the corn starch granules as lightly decomposed may well be blended with wheat flour and they are effective for improving the texture of noodle and bread.

Since the paste as prepared from the enzyme-treated starch granules is smooth and soft to the tongue, it may be blended with drinks and other foods to improve the taste of them.

Improvement of the physical properties of raw starch by acid-treatment could be anticipated. Any and every starch granules may be used, irrespective of the kind, provided that they have a starch granular structure. The method of the present invention can be applicable to of raw (or native) starch, dry heat-treated starch, alkali-treated starch and others treated by any other means.

Any kind of the enzyme to be used for the purpose of the invention if it is effective with respect to starch granules. In order to effectively lower the viscosity of the decomposed starch granules, α-amylase is preferred. The action and effect of the enzyme used also vary, depending upon the kind of the starch granules to be treated therewith. The amylase which can be used in the present invention broadly includes various kinds such as α-amylase, β-amylase, glucoamylase and raw starch decomposing enzyme. An enzyme which is suitable to provide the intended characteristics is used, and two or more different enzymes may be used in combination.

EXAMPLE 2

10 mg of α-amylase (commercial product) and 100 ml of phosphate buffer (200 mM, pH 6.9) were added to 25 g of rice starch and stirred at 30° C. to effect enzymatic reaction therebetween. After the reaction, the reaction mixture was centrifuged. The total saccharide content in the resulting supernatant was measured, and the decomposition percentage was calculated. The centrifuged starch was washed twice with 20 ml of a pure water, and 40 ml of acetone was added thereto. The whole was dehydrated and dried under reduced pressure at 40° C. overnight, and the various characteristic values of the product were measured by viscography. The results obtained are shown in Table 3 below.

As is obvious from the results in Table 3, the maximum viscosity suddenly decreased in the decomposition percentage of about 2%, but any particular deformation of the outward appearance of the decomposed product was not admitted by observation with SEM.

As a whole, glutinous rice starch granules are easily decomposable with amylase, and the amylase decomposability of nonglutinous rice starch granules varies in accordance with the kind and sort of them. In particular, a so-called high-quality rice displayed amylase decomposition resistance.

TABLE 3

| | Viscographic Characterisitic Values of α-amylase-decomposed Rice Starch Granules | | | | | | | | | |
|---|---|---|---|---|---|---|---|---|---|---|
| | Viscographic Characterisitic Values of Glucoamylase-decomposed Rice Starch Granules | | | | | | | | | |
| Variety | Decomposition Percentage (%) | Gelatinization Temperature (°C.) | Maximum Viscosity (g · cm) | Maximum Viscosity Temperature (°C.) | Minimum Viscosity (g · cm) | Minimum Viscosity Temperature (°C.) | Break-down | Final Viscosity (g · cm) | Consistency (g · cm) | Set-back (g · cm) |
| Wakaho-no-megumi | 0.0 | 70.0 | 8.2 | 87.5 | 4.1 | 96.0 | 4.1 | 10.5 | 6.4 | 4.4 |
| | 0.5 | 71.0 | 5.6 | 88.0 | 1.9 | 95.0 | 3.7 | 8.5 | 6.6 | 4.3 |

TABLE 3-continued

| | | Viscographic Characterisitic Values of α-amylase-decomposed Rice Starch Granules | | | | | | | | |
|---|---|---|---|---|---|---|---|---|---|---|
| | | Viscographic Characterisitic Values of Glucoamylase-decomposed Rice Starch Granules | | | | | | | | |
| Variety | Decomposition Percentage (%) | Gelatinization Temperature (°C.) | Maximum Viscosity (g · cm) | Maximum Viscosity Temperature (°C.) | Minimum Viscosity (g · cm) | Minimum Viscosity Temperature (°C.) | Breakdown | Final Viscosity (g · cm) | Consistency (g · cm) | Set-back (g · cm) |
| | 0.9 | 71.0 | 4.9 | 89.5 | 1.8 | 96.0 | 3.1 | 7.4 | 5.6 | 3.8 |
| | 2.2 | 68.0 | 0.6 | 71.0 | 0.0 | 95.0 | 0.6 | 0.0 | 0.0 | 0.0 |
| | 3.2 | N.D | N.D | N.D | 0.0 | 94.0 | N.D | 1.2 | 1.2 | 0.6 |
| | 5.0 | 67.0 | 0.1 | 70.0 | 0.0 | 95.0 | 0.1 | 0.0 | 0.0 | 0.0 |
| Wakaho- | 0.0 | 70.0 | 9.0 | 89.0 | 5.3 | 95.5 | 3.7 | 10.5 | 5.2 | 3.7 |
| no-minori | 0.5 | 72.0 | 4.8 | 87.0 | 1.2 | 96.0 | 3.6 | 7.1 | 5.9 | 3.8 |
| | 1.1 | 67.0 | 3.0 | 83.5 | 0.2 | 95.5 | 2.8 | 1.5 | 1.3 | 0.2 |
| | 2.2 | 57.5 | 1.1 | 74.5 | 0.0 | 95.5 | 1.1 | 0.5 | 0.5 | 0.1 |
| | 2.7 | 67.0 | 0.4 | 70.0 | 0.0 | 96.0 | 0.4 | 0.1 | 0.0 | 0.1 |
| | 4.5 | 66.0 | 0.3 | 69.0 | 0.0 | 94.5 | 0.3 | 0.1 | 0.1 | 0.1 |
| Nihonbare | 0.0 | 71.0 | 10.8 | 87.0 | 3.5 | 95.5 | 7.3 | 8.0 | 4.5 | 2.8 |
| | 0.5 | 68.0 | 5.8 | 84.0 | 0.6 | 96.0 | 5.2 | 3.4 | 2.8 | 1.8 |
| | 0.9 | 68.0 | 2.9 | 78.0 | 0.0 | 95.0 | 2.9 | 1.0 | 1.0 | 0.6 |
| | 1.9 | 67.5 | 0.8 | 73.0 | 0.0 | 96.0 | 0.8 | 0.0 | 0.0 | 0.1 |
| | 3.1 | 67.0 | 0.6 | 72.5 | 0.0 | 96.0 | 0.8 | 0.1 | 0.1 | 0.1 |
| | 5.1 | N.D | N.D | N.D | 0.0 | 94.5 | N.D | N.D | N.D | N.D |
| Koshihikar | 0.0 | 70.0 | 9.3 | 90.0 | 5.7 | 96.0 | 3.6 | 11.0 | 5.3 | 4.0 |
| | 0.4 | 69.0 | 6.6 | 87.5 | 1.5 | 95.5 | 5.1 | 5.8 | 4.3 | 2.5 |
| | 1.1 | 65.5 | 2.0 | 76.5 | 0.0 | 94.5 | 2.0 | 0.8 | 0.8 | 0.6 |
| | 1.9 | 66.0 | 0.9 | 70.0 | 0.0 | 95.0 | 0.9 | 0.1 | 0.1 | 0.0 |
| | 2.9 | 67.0 | 0.4 | 70.0 | 0.0 | 95.0 | 0.4 | 0.2 | 0.2 | 0.1 |
| | 5.2 | N.D | N.D | N.D | 0.0 | 94.5 | N.D | 0.1 | 0.1 | 0.1 |
| Michihikar | 0.0 | 60.5 | 6.9 | 67.0 | 3.6 | 94.5 | 3.3 | 6.8 | 3.2 | 1.4 |
| | 0.5 | 62.0 | 4.4 | 66.0 | 0.1 | 95.5 | 4.3 | 1.4 | 1.3 | 0.7 |
| | 1.0 | 63.5 | 1.1 | 65.5 | 0.0 | 93.0 | 1.1 | 0.2 | 0.2 | 0.2 |
| | 2.0 | 52.0 | 0.2 | 66.0 | 0.0 | 96.0 | 0.2 | 0.2 | 0.2 | 0.1 |
| | 3.0 | N.D | N.D | N.D | 0.0 | 96.0 | N.D | 0.2 | 0.2 | 0.1 |
| | 5.6 | N.D | N.D | N.D | 0.0 | 95.0 | N.D | 0.0 | 0.2 | 0.0 |

EXAMPLE 3

Enzyme-treated dry starch granules were obtained in the same manner as in Example 2, except that from 1 to 2 mg of glucoamylase of a commercial product and acetate acid buffer (200 mM, pH5.2) were used. By observation with SEM, definite holes were found in the decomposed product with a decomposition percentage of 1%. The size of each hole was different from that in the α-amylase-decomposed product and was sharp.

Various viscographic characteristic values of the decomposed starch granules are shown in Table 4 below. As is obvious therefrom, any particular change of the viscosity characteristic is not admitted in the decomposition percentage of about 3 % or so. With further progress of the decomposition of starch granules, elevation of the gelatinization temperature is admitted.

The glucoamylase-treated starch granules displayed a property of well adsorbing oily substances.

TABLE 4

| | Viscographic Characterisitic Values of Glucoamylase-decomposed Rice Starch Granules | | | | | | | | |
|---|---|---|---|---|---|---|---|---|---|
| Variety | Decomposition Percentage (%) | Gelatinization Temperature (°C.) | Maximum Viscosity (g · cm) | Maximum Viscosity Temperature (°C.) | Minimum Viscosity (g · cm) | Minimum Viscosity Temperature (°C.) | Breakdown | Final Viscosity (g · cm) | Consistency (g · cm) | Set-back (g · cm) |
| Wakaho- | 0.0 | 70.0 | 8.2 | 87.5 | 4.1 | 96.0 | 4.1 | 10.5 | 6.4 | 4.4 |
| no-megumi | 0.5 | 74.0 | 8.3 | 89.0 | 5.1 | 96.0 | 3.2 | 10.2 | 5.1 | 3.9 |
| | 2.5 | 74.0 | 6.9 | 90.5 | 4.1 | 96.0 | 2.8 | 9.6 | 5.5 | 4.2 |
| | 5.2 | 75.0 | 7.0 | 89.0 | 4.3 | 95.0 | 2.7 | 10.2 | 5.9 | 4.2 |
| | *30.8 | 85.0 | 7.0 | 92.0 | 4.2 | 96.0 | 2.8 | 8.1 | 3.9 | 2.6 |
| Wakaho- | 0.0 | 70.0 | 9.0 | 89.0 | 5.3 | 95.5 | 3.7 | 10.5 | 5.2 | 3.7 |
| no-minori | 4.9 | 70.0 | 9.1 | 90.0 | 5.4 | 96.0 | 3.7 | 11.3 | 5.9 | 4.2 |
| Nihonbare | 0.0 | 71.0 | 10.8 | 87.0 | 3.5 | 95.5 | 7.3 | 8.0 | 4.5 | 2.8 |
| | 7.2 | 80.0 | 8.4 | 92.0 | 3.4 | 95.0 | 5.0 | 8.4 | 5.0 | 3.6 |
| Koshihikar | 0.0 | 70.0 | 9.3 | 90.0 | 5.7 | 96.0 | 3.6 | 11.0 | 5.3 | 4.0 |
| | 0.5 | 78.0 | 8.2 | 89.0 | 3.6 | 94.0 | 4.6 | 8.5 | 5.0 | 3.2 |
| | 6.0 | 79.5 | 8.4 | 91.0 | 3.6 | 95.0 | 4.8 | 8.6 | 5.0 | 3.5 |
| Michihikar | 0.0 | 60.5 | 6.9 | 67.0 | 3.6 | 94.5 | 3.3 | 6.8 | 3.2 | 1.4 |
| | 6.2 | 60.0 | 6.7 | 65.0 | 3.3 | 94.0 | 3.4 | 6.0 | 2.7 | 2.2 |

(*) Industrial crude enzyme liquid was used.

EXAMPLE 4

Corn starch granules were treated and decomposed with α-amylase in a decomposition percentage of from 0.5 to 1.0% to obtain decomposed starch granules having a larger final viscosity and a larger consistency value than those of the original starch granules. Because of the properties of the decomposed starch granules, they can be added to various starch foods so as to tighten the taste of them.

As has been explained in detail above, starch granules are treated with various amylases in accordance with the present invention to modify the characteristics of them. In particular, where cereal starch granules are lightly decomposed with α-amylase, the viscosity characteristic of them greatly varies so that the viscosity of the decomposed granules decreases to such a degree that they are only slightly viscous. Therefore, the decomposed starch granules may be used-in preparing instant liquid foods, and the use of them is expected to be extremely broad. By appropriately blending the decomposed starch granules and other non-treated starch granules or decomposed starch granules, blends of different starch granules having various viscosity values can be obtained. Since the paste or liquid to be prepared from enzyme-treated starch granules is smooth and soft to the touch, they may be expected to be useful as base materials for producing various foods.

Starch granules with holes have an interesting characteristic of adsorbing aromatic components. Amylases are expected to decompose preferentially the hydrophilic parts of starch granules, whereupon the hydrophobic parts of them remains to give a result that the decomposed starch granules adsorb hydrophobic substances such as aromatic components. Enzyme-treated starch granules into which aromatic components have been introduced may be combined with other enzyme-treated low-viscosity starch granules to produce various foods.

Since enzyme-treated low-viscosity starch granules may be produced extremely simply, they are useful as a raw material in the starch sugar industry. The concentration of a substrate of enzyme-treated starch granules having a low viscosity can be elevated and even though the temperature thereof is lowered to a suitable temperature for the enzymatic reaction, the liquefied starch is not gelatinized. Therefore, continuous addition of the substrate is possible and the enzyme-treated low-viscosity starch granules may be utilized in the process of continuous production of starch sugar.

While the invention has been described in detail and with reference to specific embodiments thereof, it will be apparent to one skilled in the art that various changes and modifications can be made therein without departing from the spirit and scope thereof.

What is claimed is:

1. A method of producing corn starch granules having a decomposition percentage of 0.1 to 1.0% which comprises contacting corn raw starch granules with an $\alpha$-amylase in water or a buffer solution at a temperature of 10° to 65° C. for 1 to 4 hours, to obtain said starch granules having said decomposition percentage.

2. The method as claimed in claim 1, wherein the raw corn starch granules are contacted in a buffer selected from the group consisting of a phosphoric acid buffer having a pH of 6.9, an acetic acid buffer having a pH of 5.2 and an acetic acid buffer having a pH of 4.8.

3. The method as claimed in claim 1, wherein the concentration of the corn starch granules in said water or buffer solution is from 5 to 40%.

4. The method as claimed in claim 3, wherein the temperature is 25° to 40° C.

5. A method as claimed 4, wherein the $\alpha$-amylase is in an amount of 4 to 40 IU per gram of the corn starch granules.

6. The method as claimed in claim 1, wherein the decomposition percentage is 0.6%.

7. The method as claimed in claim 1, wherein the $\alpha$-amylase is in an amount of 0.4 to 400 IU.

* * * * *